US008025052B2

(12) United States Patent
Matthews et al.

(10) Patent No.: US 8,025,052 B2
(45) Date of Patent: Sep. 27, 2011

(54) SYSTEM AND METHOD OF MONITORING RESPIRATORY EVENTS

(75) Inventors: Greg Matthews, Pittsburgh, PA (US); Leonardo A. Baloa, Pittsburgh, PA (US)

(73) Assignee: Ric Investments, LLC, Wilmington, DE (US)

( * ) Notice: Subject to any disclaimer, the term of this patent is extended or adjusted under 35 U.S.C. 154(b) by 297 days.

(21) Appl. No.: 11/600,981

(22) Filed: Nov. 17, 2006

(65) Prior Publication Data
US 2007/0113849 A1    May 24, 2007

Related U.S. Application Data

(60) Provisional application No. 60/738,529, filed on Nov. 21, 2005.

(51) Int. Cl.
*A61M 16/00* (2006.01)
*F16K 31/00* (2006.01)

(52) U.S. Cl. ......... 128/204.21; 128/204.22; 128/204.23; 128/204.26

(58) Field of Classification Search ............. 128/200.24, 128/204.21, 204.22, 204.23, 920, 898, 204.24, 128/204.26; 600/529, 534
See application file for complete search history.

(56) References Cited

U.S. PATENT DOCUMENTS

| | | | | |
|---|---|---|---|---|
| 5,245,995 A * | 9/1993 | Sullivan et al. | ........... | 128/204.23 |
| 5,313,937 A * | 5/1994 | Zdrojkowski | ............ | 128/202.22 |
| 5,335,654 A * | 8/1994 | Rapoport | ................ | 128/204.23 |
| 5,447,525 A | 9/1995 | Powell et al. | | |
| 5,458,137 A * | 10/1995 | Axe et al. | ................. | 128/204.23 |
| 5,535,739 A * | 7/1996 | Rapoport et al. | ........ | 128/204.23 |
| 5,652,296 A | 7/1997 | Randen | | |
| 5,704,923 A | 1/1998 | Chiu-Hsiung et al. | | |
| 5,823,187 A * | 10/1998 | Estes et al. | ............... | 128/204.23 |
| 5,931,160 A * | 8/1999 | Gilmore et al. | .......... | 128/204.21 |
| 6,017,315 A | 1/2000 | Starr et al. | | |
| 6,029,665 A * | 2/2000 | Berthon-Jones | ......... | 128/204.23 |
| 6,085,747 A * | 7/2000 | Axe et al. | ................. | 128/204.23 |
| 6,138,675 A * | 10/2000 | Berthon-Jones | ......... | 128/204.23 |
| 6,401,713 B1 * | 6/2002 | Hill et al. | ................. | 128/204.21 |
| 6,436,053 B1 * | 8/2002 | Knapp et al. | .................. | 600/538 |
| 6,463,930 B2 * | 10/2002 | Biondi et al. | ............ | 128/204.21 |
| 6,488,634 B1 * | 12/2002 | Rapoport et al. | ............. | 600/538 |
| 6,626,175 B2 * | 9/2003 | Jafari et al. | .............. | 128/204.21 |

(Continued)

FOREIGN PATENT DOCUMENTS

WO    WO 03030804 A2 *    4/2003

OTHER PUBLICATIONS

"Sleep-Related Breathing Disorders in Adults: Recommendations for Syndrome Definition and Measurement Techniques in Clinical Research", Apr. 1999.

*Primary Examiner* — Justine Yu
*Assistant Examiner* — Clinton Ostrup
(74) *Attorney, Agent, or Firm* — Michael W. Haas

(57) ABSTRACT

A system and method of monitoring a patient, that in one embodiment, comprises determining a flow of gas generated by respiration of the patient, identifying a respiratory event entry and a respiratory event exit based on the flow of gas generated by respiration of the patient, and identifying a respiratory event when the identification of the respiratory event entry is followed by the identification of respiratory event exit.

17 Claims, 4 Drawing Sheets

U.S. PATENT DOCUMENTS

| | | |
|---|---|---|
| 6,731,984 B2 | 5/2004 | Cho et al. |
| 6,793,629 B2 | 9/2004 | Rapoport et al. |
| 6,920,887 B2 | 7/2005 | Lo |
| 6,988,994 B2 | 1/2006 | Rapoport et al. |
| 7,168,429 B2 * | 1/2007 | Matthews et al. ........ 128/204.21 |
| 2002/0088465 A1 * | 7/2002 | Hill ........................ 128/204.23 |
| 2003/0111079 A1 | 6/2003 | Matthews et al. |
| 2004/0187870 A1 * | 9/2004 | Matthews et al. ........ 128/204.21 |
| 2006/0009708 A1 | 1/2006 | Rapoport et al. |
| 2006/0102179 A1 | 5/2006 | Rapoport et al. |
| 2007/0062533 A1 * | 3/2007 | Choncholas et al. .... 128/204.23 |

* cited by examiner

SYSTEM AND METHOD OF MONITORING RESPIRATORY EVENTS

CROSS-REFERENCE TO RELATED APPLICATIONS

This application claims priority under 35 U.S.C. §119(e) from provisional U.S. patent application No. 60/738,529 filed Nov. 21, 2005, the contents of which are incorporated herein by reference.

BACKGROUND OF THE INVENTION

1. Field of the Invention

The invention relates to respiratory treatment systems.

2. Description of the Related Art

Patients that suffer from sleep breathing disorders, such as obstructive sleep apnea (OSA), cheyne-stokes respiration, central apneas, or upper airway resistance syndrome (UARS), experience respiratory events during sleep. A respiratory event caused by OSA or UARS is usually characterized by a flow limitation in which the patient's upper airway becomes obstructed or restricted. During the respiratory event, the flow limitation causes the flow of gas through the airway to decrease progressively often until a respiratory effort related arousal occurs. The arousal clears the airway and the patient can experience inhalations and expirations that are abnormally large and sharp in relation to the patient's normal breathing flow.

In order to detect these types of respiratory events caused by upper airway restrictions, a signal representative of a rate of the flow of gas in an airway of a patient is typically monitored for changes that represent a flow limitation in the airway of the patient. Conventional methods of monitoring the flow rate to detect a flow limitation include analyzing the signal for a shape and/or pattern that is expected to be symptomatic of a flow limitation within the patient's airway, an absolute measurement of the signal, or relative changes in the flow rate. However, monitoring the flow of gas to the airway of the patient to detect flow limitations may lead to erroneous detections of respiratory events, and some respiratory events may not be detected at all. Consequently, a need exists for monitoring a patient for respiratory events with an enhanced accuracy.

SUMMARY OF THE INVENTION

Accordingly, it is an object of the present invention to provide a method of monitoring a patient that overcomes the shortcomings of conventional monitoring methods. This object is achieved according to one embodiment of the present invention by providing a method that includes (1) monitoring a parameter associated with a flow of gas generated by respiration of the patient, (2) identifying a respiratory event entry based on the parameter, (3) identifying a respiratory event exit based on the determination of the flow of gas generated by respiration of the patient, and (4) identifying a respiratory event when the identification of the respiratory event entry is followed by the identification of respiratory event exit.

Another aspect of the invention relates to a method of monitoring a patient. In one embodiment the method comprises determining a flow of gas generated by respiration of the patient, identifying a respiratory event based on an increase in the peak flow of the gas during consecutive inspirations, and adjusting one or more aspects of treatment received by the patient based on the identification of the respiratory event.

Another aspect of the invention relates to a patient treatment system that delivers a pressurized flow of breathable gas to an airway of a patient. In one embodiment, the system comprises a flow sensor, an event entry module, an event exit module, and a respiratory event module. The flow sensor detects a flow of breathable gas generated by respiration of the patient. The event entry module that identifies respiratory event entries based on the detection of the flow of gas generated by respiration of the patient. The event exit module that identifies respiratory event exits based on the detection of the flow of gas generated by respiration of the patient. The respiratory event module that identifies a respiratory event when an identification of a respiratory event entry is followed by an identification of a respiratory event exit.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
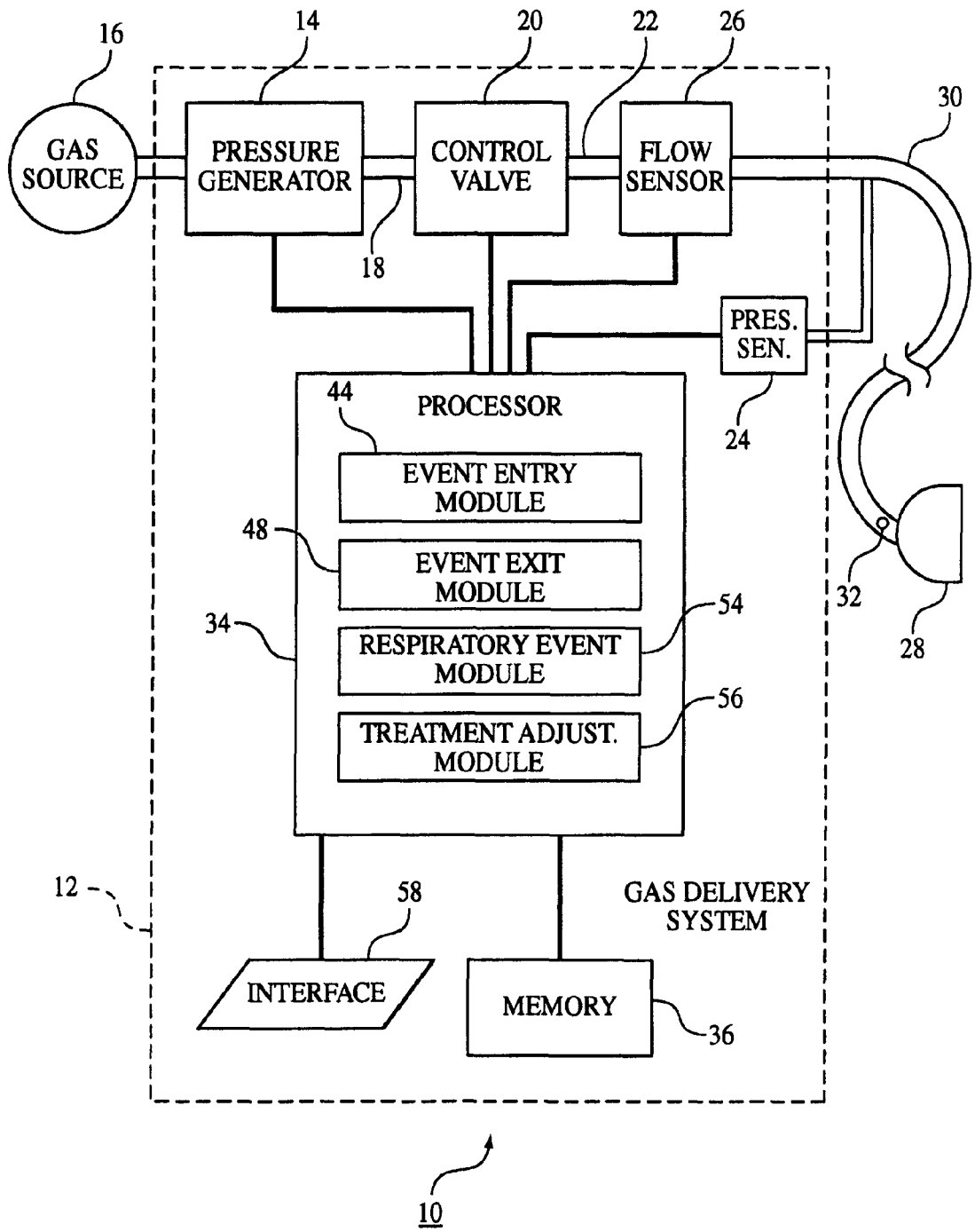
FIG. 1 illustrates a patient treatment system according to one embodiment of the invention.

FIG. 1 schematically illustrates an exemplary embodiment of a patient treatment system 10 according to the principles of the present invention. Patient treatment system 10 is capable of providing and automatically controlling the pressure of a gas delivered to a patient. Patient treatment system 10 includes a gas delivery system 12 that controls the flow and/or pressure of breathing gas provided to the patient. Gas delivery system 12 includes a pressure generator 14 that receives a supply of breathable gas from a breathable gas source 16, and elevates the pressure of that gas for delivery to the airway of a patient. Pressure generator 14 may include any device, such as a blower, piston, or bellows that is capable of elevating the pressure of the received breathable gas from source 16 for delivery to a patient. In one embodiment of the present invention, pressure generator 14 is a blower that is driven at a constant speed during the course of the pressure support treatment to produce a constant pressure or flow rate at its output 18.

According to one embodiment, gas source 16 is simply atmospheric air drawn into the system by pressure generator 14. In another embodiment, gas source 16 comprises a tank of pressurized gas connected with pressure generator 14. The tank of gas can contain any breathable gas, such as oxygen, air, or other mixture of breathable gas. The present invention also contemplates that a separate gas source 16 need not be used, but instead the pressure generator 14 can itself be defined by a canister or tank of pressurized gas, with the pressure delivered to the patient being controlled by a pressure regulator. In addition, while the embodiment of FIG. 1 illustrates a separate gas source 16, the present invention contemplates that gas source 16 can be considered to be part of the gas delivery system 12.

Additionally, in another embodiment, the gas source 16 can be provided in the same housing as the rest of the gas delivery system 12. In yet another embodiment, an external gas source 16 provides the pressurized flow of breathable gas so as to constitute a pressure generator, thus eliminating the need for the separate pressure generator 14.

In the illustrated embodiment, gas delivery system 12 includes a control valve 20. The gas is delivered to control valve 20, with an elevated pressure, downstream of the pressure generator 14. Control valve 20, either alone or in combination with pressure generator 14, controls the final pressure or flow of gas 22 exiting the gas delivery system 12. Examples of a suitable control valve 20 include at least one valve, such as sleeve or poppet valve that exhausts gas from the patient circuit as a method of controlling the pressure in the patient circuit. U.S. Pat. No. 5,704,923 to Hete et al., the contents of which are incorporated herein by reference, teaches a dual poppet valve system suitable for use as control valve 20 that exhausts gas to atmosphere and restricts the flow of gas from the pressure generator 14 to the patient. Other suitable pressure/flow controllers are well known to those skilled in the art.

In embodiments in which pressure generator 14 is a blower that operates at all times at one speed and control valve 20 alone controls the final pressure and/or flow rate for gas 22 output from control valve 20. However, as noted above, the present invention also contemplates controlling the operating speed of pressure generator 14 in combination with control valve 20 to control the final pressure and flow rate of the breathable gas that is output by system 12 for delivery to the patient. For example, a pressure or flow rate close to the desired pressure or flow rate can be set by establishing an appropriate operating speed for pressure generator 14 along and by setting the opening in control valve 20 so that the two, operating together, determine the final pressure for the breathable gas 22. The present invention also contemplates eliminating control valve 20 and controlling the pressure and/or the flow of gas delivered to the patient based only on the operation of pressure generator 14.

The pressure of the flow of breathable gas is detected by a pressure sensor 24. In the embodiment of FIG. 1, pressure sensor 24 is a single sensor unit disposed downstream of pressure generator 14 and control valve 20. However, in other embodiments, pressure sensor 24 may include a single sensor unit disposed elsewhere, such as at an inlet of control valve 20, or at a location downstream from gas delivery system 12. Alternatively, pressure sensor 24 may include a plurality of sensor units disposed at various locations within gas delivery system 12. Pressure sensor 24 may include any device, transducer, or devices, capable of detecting the pressure of the pressurized flow of breathable gas generated by gas delivery system 12.

In the embodiment of FIG. 1, patient treatment system 10 includes a flow sensor 26. The pressurized flow of breathable gas 22 output from control valve 20 is delivered to flow sensor 26, which detects the instantaneous volume (V) of gas generated by respiration of the patient, and/or the instantaneous flow rate (V') of such gas to the patient, or both. Flow sensor 26 may include any device suitable for detecting these parameters, such as a spirometer, pneumotach, variable orifice transducer, or other conventional flow transducer. It is also known to measure flow based on the operating speed of the pressure generator or the position of the control valve. In the illustrated embodiment, flow sensor 26 is provided in the gas delivery system away from the patient. If the flow at the airway of the patient is needed, it can be estimated, using conventional techniques, based on the known pressure drop of the patient circuit and based on determination of leaks generated by exhaust port 32 and patient interface assembly 28.

The present invention also contemplates providing the flow sensor at or near a patient interface assembly 28, which communicates the pressurized flow of breathable gas with the airway of the patient. For example, U.S. Pat. No. 6,017,315 to Starr et al., the contents of which are incorporated herein by reference, teaches a quantitative flow member that is located at the patient interface assembly 28. The present invention also contemplates locating sensor 26 at any location along a patient circuit 30, as will be described.

The flow of breathing gas is carried from gas delivery system 12 to the patient via a patient circuit 30, which can be a single flexible conduit that carries the flow of breathing gas to a patient interface assembly 28. Alternatively, as described later, the patient circuit may be a two-limb circuit. Patient interface assembly 28 may include any non-invasive patient interface appliance for communicating the pressurized flow of breathable gas to the airway of the patient. For example, patient interface assembly 28 may include a nasal mask, nasal/oral mask, total face mask, or nasal cannula. Patient interface assembly 28 may also include a headgear assembly, such as mounting straps or a harness, for removing and fastening the patient interface appliance to the patient.

In the illustrated embodiment, the patient interface assembly 28 and/or patient circuit 30 includes a suitable exhaust port 32 for exhausting gas from these components to ambient atmosphere. In an exemplary embodiment, exhaust port 32 is a passive exhaust port in the form of a continuously open port that imposes a flow restriction on the exhaust gas to permit control of the pressure of gas within patient interface assembly 28. It is to be understood, however, that exhaust port 32 can be an active exhaust port that assumes different configurations to control the exhaust rate. Examples of suitable exhaust ports are taught, for example, in U.S. Pat. Nos. 5,652,296 and 5,447,525 both to Zdrojkowski et al.

As shown, gas delivery system 12 includes a processor 34 that controls various operating aspects of the gas delivery system. For example, the output of flow sensor 26 and pressure sensor 24 are provided to processor 34. The processor uses this information to determine the pressure of the gas, the instantaneous volume (V) of the pressurized flow of the gas, and/or the instantaneous flow rate (V') of the gas. In some instances, processor 34 determines the instantaneous volume by integrating the flow rate detected by flow sensor 26. Because, in one embodiment, flow sensor 26 may be located relatively far from patient interface assembly 28, in order to determine the actual flow rate of gas to the patient taking into account, for example, leaks in patient circuit 30 and elsewhere in patient delivery system 10, processor 34 may receive the output from flow sensor 26 as an estimated patient flow.

The processor 34 processes this estimated flow information, for example, by performing leak estimation, to determine the flow of gas generated by respiration of the patient, as is known to those skilled in the art.

Processor 34 controls pressure generator 14 and the actuation of control valve 20, thereby controlling the pressure of the pressurized flow of gas generated by gas delivery system 12. In one embodiment, processor 34 comprises a processor that is suitably programmed with an algorithm or algorithms to calculate the pressure to be applied to the patient according to one of any one of various modes of ventilation. In addition, processor 34 may be capable of controlling pressure generator 14 and/or control valve 20 based on data received from pressure sensor 24 and/or flow sensor 26 to apply the calculated pressure to the breathable gas within gas delivery system 12. In one embodiment of the present invention, the gas delivery system 12 includes a memory 36 associated with processor 34 for storing the programming used to perform any of a plurality of modes of ventilation, depending on which mode of ventilation is selected by the caregiver or patient using control interface 58. Memory 36 may also be capable of storing data regarding the operation of the gas delivery system 12, input commands, alarm thresholds, as well as any other information pertinent to the operation of the gas delivery system 12, such as detected values of gas flow, volume, pressure, device usage, operating temperatures, and motor speed.

In one embodiment, processor 34 identifies respiratory events including, for example, upper airway resistance, upper airway collapse, upper airway blockage, or another respiratory event. In the embodiment shown in FIG. 1, processor 34 comprises an event entry module 44 that identifies when the patient is entering a respiratory event based on the detection of the flow of gas generated by respiration of the patient taken by flow sensor 26. In one embodiment, the detection of the flow of gas generated by respiration of the patient includes a determination of the flow rate. In another embodiment, the detection of the flow of gas includes a determination of the volume of the flow of gas.

Figure 2:
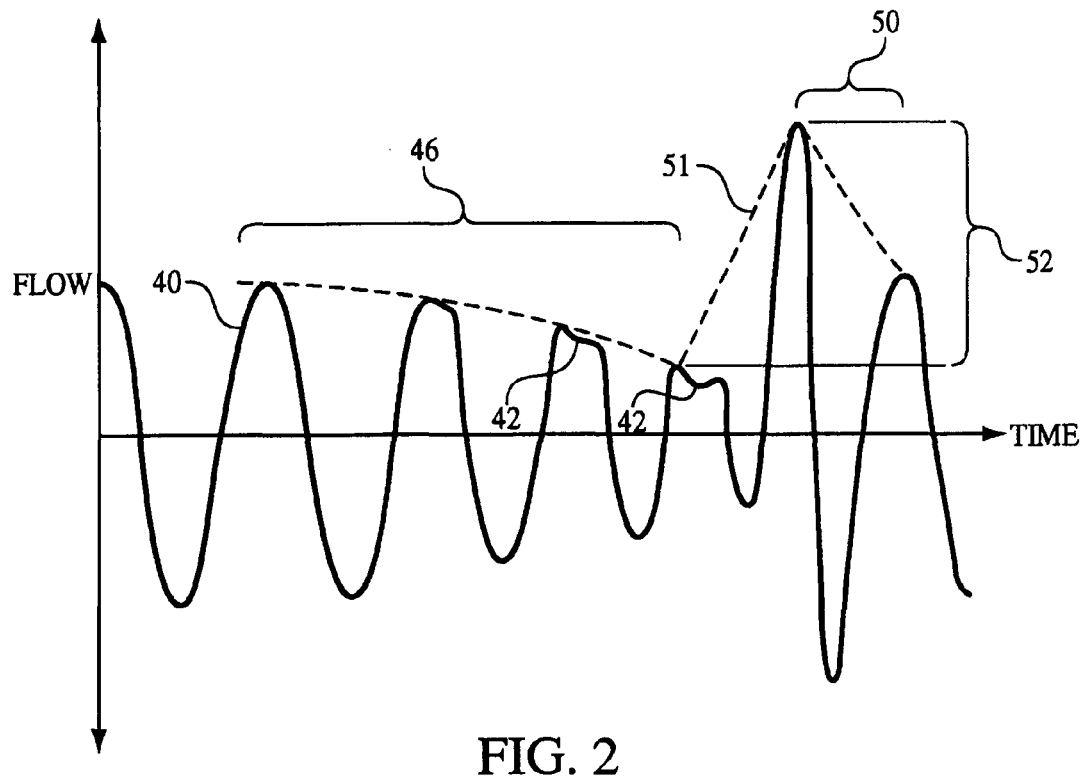
FIG. 2 illustrates an exemplary flow waveform generated by a flow sensor in accordance with one embodiment of the invention.

The identification of respiratory event entries, and/or other respiratory circumstances of the patient, may be based on a signal generated by flow sensor 26 that represents the flow of gas generated by respiration of the patient. FIG. 2 illustrates a waveform 40 that corresponds to the flow measured by the flow sensor. The peaks of waveform 40 represent the flow of gas generated by inspirations of the patient, and the troughs of waveform 40 represent the flow of gas generated by exhalations of the patient.

In one embodiment, event entry module 44 identifies an entry into a respiratory event based on the shape of the peaks and/or the troughs of waveform 40. More particularly, a flattening 42 of waveform 40 during inspiration indicates a "flow limitation," or blockage, within the airway causing the onset of a respiratory event. In another embodiment, event entry module 44 identifies an entry into a respiratory event based on an observed pattern of relative fluctuations in the magnitude of the peaks and/or troughs of waveform 40. More particularly, as the peak flow of gas generated by inspiration gradually decreases, event entry module 44 identifies an event entry based on a comparison between a most recent inspiration peak and a predetermined number of previous inspiration peaks. In FIG. 2, this decrease in the peak flow of gas generated by inspirations of the patient is represented by the gradual decline in the magnitude of the peaks of waveform 40 within a region 46 of the waveform. In one embodiment of the invention event entry module 44 may identify an entry into a respiratory event based on both shape of waveform 40 during inspiration and on relative changes in the size (magnitude) of the peaks of waveform 40 that represent the flow of gas during inspiration by the patient.

As is shown in FIG. 1, processor 34 comprises an event exit module 48 that identifies respiratory effort related arousals that denote an exit from a respiratory event, or respiratory event exit. In one embodiment of the invention, event exit module 48 identifies an event exit (or arousal) based on an observed pattern of relative fluctuations in the flow of gas during inspiration by the patient. Turning to FIG. 2, section 50 of waveform 40 includes a pattern that is indicative of the relatively sharp, large inhalation(s) typically experienced by the patient during a respiratory event exit. In order to identify the pattern of the flow of gas generated by respiration of the patient associated with an event exit, in one embodiment, event exit module 48 compares the peak flow of the flow of gas generated during successive inspirations, and identifies an event exit when the determined flow indicates a general decline in the flow of gas during inspirations followed by a rapid increase in the flow of gas during inspiration. In FIG. 2, a plot 51 of the peak flow of waveform 40 serves to emphasize this pattern.

In another embodiment, event exit module 48 detects an event exit, or arousal, based on a difference in the flow of gas generated by consecutive inspirations of the patient. For example, if a first peak in waveform 40 associated with a first inspiration is smaller in magnitude than a second peak in waveform 40 associated with a next inspiration by greater than a threshold amount, event exit module detects a respiratory effort response arousal (RERA) indicative of an event exit. This comparison is represented in FIG. 2 as a difference 52 between successive peaks of waveform 40. In one embodiment, event exit module 48 first monitors waveform 40 for the pattern in the flow of gas to generated by respiration of the patient, described above, that indicates a respiratory effort related arousal, and then identifies an event exit if the difference in magnitude of consecutive peaks of waveform 40 that form the observed pattern are greater than a threshold value.

It will be appreciated that other paradigms and/or criteria for analyzing fluctuations in the flow detected by flow sensor 26 to identify respiratory effort related arousals indicative of respiratory event exits may be implemented by event exit module 48. For example, in one embodiment, event exit module 48 identifies event exits based on the absolute magnitude of the flow detected by flow sensor 26 and/or changes in the shape of waveform 40 generated based on an output of flow sensor 26. In another embodiment, event exit module 48 identifies respiratory event exits based on the peak flow. Further, it may be appreciated that although event entry module 44 and event exit module 48 have been described above as detecting respiratory event entries and exits based on the flow of gas generated by respiration of the patient during inspiration, the scope of the invention encompasses embodiments in which expiratory flows are implemented instead.

Returning to FIG. 1, processor 34 comprises a respiratory event module 54 that identifies a respiratory event when an identification of a respiratory event entry is followed by an identification of a respiratory event exit associated with a respiratory effort related arousal. In one embodiment, respiratory event module 54 communicates with event entry module 44 and event exit module 48, and identifies a respiratory event when event exit module 48 identifies a respiratory effort related arousal immediately following an identification of a respiratory event entry by event entry module 44.

As is shown in FIG. 1, processor 34 comprises a treatment adjustment module 56 that adjusts one or more aspects of treatment received by the patient based on the identification of a respiratory event. In one embodiment, treatment adjustment module 56 communicates with respiratory event module 54, and adjusts one or more aspects of treatment when respiratory event module 54 identifies a respiratory event. For example, treatment adjustment module 56 may adjust the pressure of the gas delivered to the patient by gas delivery system 12. In one embodiment, the pressure is increased to provide enhanced support to the airway of the patient if respiratory events are detected. The pressure may be increased to a predetermined level or by a predetermined increment. In another embodiment, the pressure is decreased to provide reduced pressure support to the airway of the patient if respiratory events are not detected. The decrease can take place automatically if, for example, no events are detected within a certain time frame while the patient is being monitored. The pressure may be decreased to a predetermined level or by a predetermined decrement.

The present invention also contemplates that the level or the amount of the pressure adjustment can be variable. For example, the level or amount of pressure adjustment can be based on the characteristic of the respiratory event. For example, the present invention contemplates monitoring the magnitude of the peak of the gas flow waveform generated during an event exit, i.e., during section 50 of waveform 40 in FIG. 2. The magnitude of this peak during one respiratory event or multiple respiratory events can be monitored and used to determine the pressure level to be applied to the patient. If, for example, the magnitude of the peaks flow over one or more event exits has been relatively large, the present invention contemplates increasing the pressure by a greater amount than if the magnitude of the peak flow over the event exits was smaller. This results in a more aggressive treatment of the patient to counteract the respiratory events. Conversely, if the magnitude of the peaks flow over one or more event exits has been relatively small, the pressure can be increased by a smaller amount.

The level or amount of pressure adjustment can also be based on the current operating condition of the gas delivery system. For example, the if the gas delivery system is operating at a relatively high pressure, the amount of pressure increase that is to be applied to the patient as a result of detecting a respiratory event can be less than if the if the system is currently delivery a relatively low pressure to the patient.

The present invention still further contemplates using the detecting of RERA events (or the lack of detection of RERA events during a certain time period) to suspend or alter other pending/ongoing therapy actions. For example, the present invention contemplates shortening or increasing a pressure ramp, changing the type of pressure therapy being delivered, changing the auto-titration parameters, or any combination thereof depending on whether or not respiratory events are detected. In one exemplary embodiment, the pressure therapy is switched from a bilevel, C-Flex™, Bi-Flex®, or PAP® therapies to a CPAP therapy if respiratory events are detected, and vice versa. Of course, the present invention also contemplates switching between any of these modes of pressure support, or even other modes of ventilating a patient, depending on the respiratory events detected. Each of these therapies are well known in the art.

In another exemplary embodiment, the present invention contemplates providing an auto-titration pressure support therapy, in which the pressure delivered to the patient varies based on the monitored condition of the patient, and using the respiratory event detection of the present invention to alter the auto-titration pressure control technique. For example, U.S. Pat. No. 6,920,887 teaches an auto-titration technique that includes conducting a $P_{opt}$ and/or $P_{crit}$ search to determine the optimum pressure to deliver to the patient. The present invention contemplates using the respiratory event detection described herein, either alone or in combination with other factors, to determine whether to initiate a $P_{opt}$ and/or $P_{crit}$ search or to terminate any such search. U.S. patent application Ser. No. 10/268,406 (publication no. US-2003-0111079-A1) teaches auto-titration techniques that include pressure ramps, statistical analysis, and decision points as to when and how to control the auto-titration algorithm. The present invention contemplates using the respiratory event detection described herein, either alone or in combination with other factors, to change the operation of the algorithm. For example, if RERA events are detected, the slope of a pressure ramp can be changed, the controller can switch to different control modules, change the threshold values to make the system more or less sensitive, and so on.

It should be appreciated that identification of a respiratory event by respiratory event module 54 may trigger any number of actions and/or operations by processor 34. For instance, in one embodiment, information corresponding to waveform 40 (e.g., a plot of the peak flow of waveform 40, numerical data reflecting the data of waveform 40, etc.) generated based on an output of flow sensor 26 during the identified respiratory event is stored. The information may be stored in memory 36. In one embodiment, the information may be reported to an interested individual (e.g., the patient, a caregiver, an insurance provider, etc.) as documentation of the respiratory event. In another embodiment, processor 34 may generate and/or record other information related to the respiratory event. For example, the number of identified respiratory events may be counted, an alarm or alert may be activated when a threshold amount of respiratory events are identified, an alarm or alert may be activated for each identified respiratory event, or other actions or operations may be executed.

It may further be appreciated that the various modules 44, 48, 54, and 56 of processor 34 may be implemented in hardware, software, firmware, or in some combination of hardware, software, and/or firmware. Additionally, although modules 44, 48, 54, and 56 are shown in FIG. 1 as being located in a single location, this need not be the case. In one embodiment, processor 34 is a plurality of separate processors located remotely from each other operating in conjunction, for example, over a network. In such an embodiment, some or all of modules 44, 48, 54, and 56 may be located remotely from each other.

A control interface 58 provides data and commands to processor 34 of gas delivery system 12. Control interface 58 may include any device suitable to provide information and/or commands to processor 34 via a hardwire or wireless connection. Typical examples of control interface 58 may include a keypad, keyboard, touch pad, mouse, microphone, switches, button, dials, or any other devices that allow a user to input information to the gas delivery system 12. Control interface 58 may also include one or more devices suitable to provide information related to patient treatment system 10 to an individual (e.g., a patient, a caregiver, etc.) such as, for example, a screen, a printer, one or more indicator light, a speaker, or other devices that enable the provision information to the individual. For example, treatment reports generated by processor 34 may be communicated via control interface 58. It should be appreciated that control interface 58 may be located at gas delivery system 12 or may be located remotely and communicate with processor 34 via an operative communications link (e.g., hardwired, wireless, etc.). In one embodiment, control interface 58 may be implemented as a Graphical User Interface (GUI) running on a computing terminal that communicates with processor 34 via a network, or other communications link.

The present invention contemplates that in an embodiment (not illustrated), patient circuit 26 can be a two-limb circuit, which is common in conventional ventilators. In a two-limb circuit, the first limb, like patient circuit 26, delivers breathing gas to the patient, except that it lacks an exhaust port. Instead, the second limb carries the exhaust gases from the patient to ambient atmosphere. Typically, an active exhaust port in the second limb under the control of a processor (e.g. processor 34) provides the desired level of positive end expiratory pressure (PEEP) to the patient.

Figure 3:
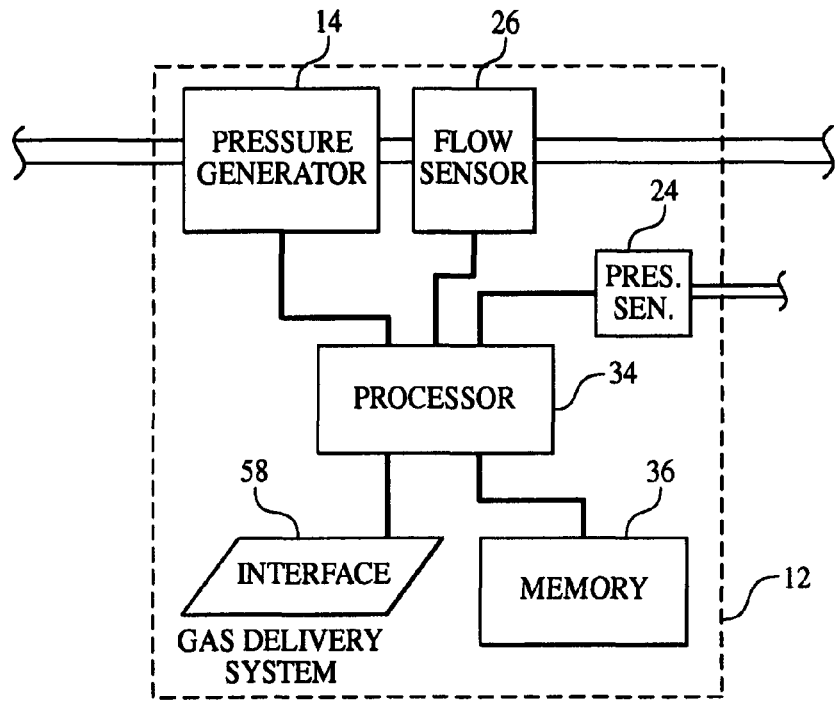
FIG. 3 illustrates a gas delivery system according to one embodiment of the invention.

An alternative embodiment of gas delivery system 12 is discussed below with reference to FIG. 3. In FIG. 3, parts similar to corresponding parts in the embodiment of FIG. 1 are labeled with the same reference numerals. Unlike the embodiment of FIG. 1, the final pressure of the gas delivered to the patient is not controlled by a control valve, either alone or in combination with pressure generator 14. Instead, gas delivery system 12 controls the pressure of the breathable gas based only on the output of a pressure generator 14. For example, in one embodiment, pressure generator 14 is a blower and processor 34 (as described in the first embodiment) controls the pressure of the breathable gas delivered to the patient by controlling the motor speed of pressure generator 14. The present invention contemplates implementing the pressure of the breathable gas as detected by pressure sensor 24 and a speed monitor for the blower motor to provide feedback data to processor 34 for controlling the operation of pressure generator 14.

In addition, the present invention contemplates that gas delivery system 12 (as shown in either of FIG. 1 or 3) and related components may include other conventional devices and components, such as a humidifier, heater, bacteria filter, temperature sensor, humidity sensor, and a gas sensor (e.g., a capnometer), that filter, measure, monitor, and analyze the flow of gas to or from the patient.

Figure 4:
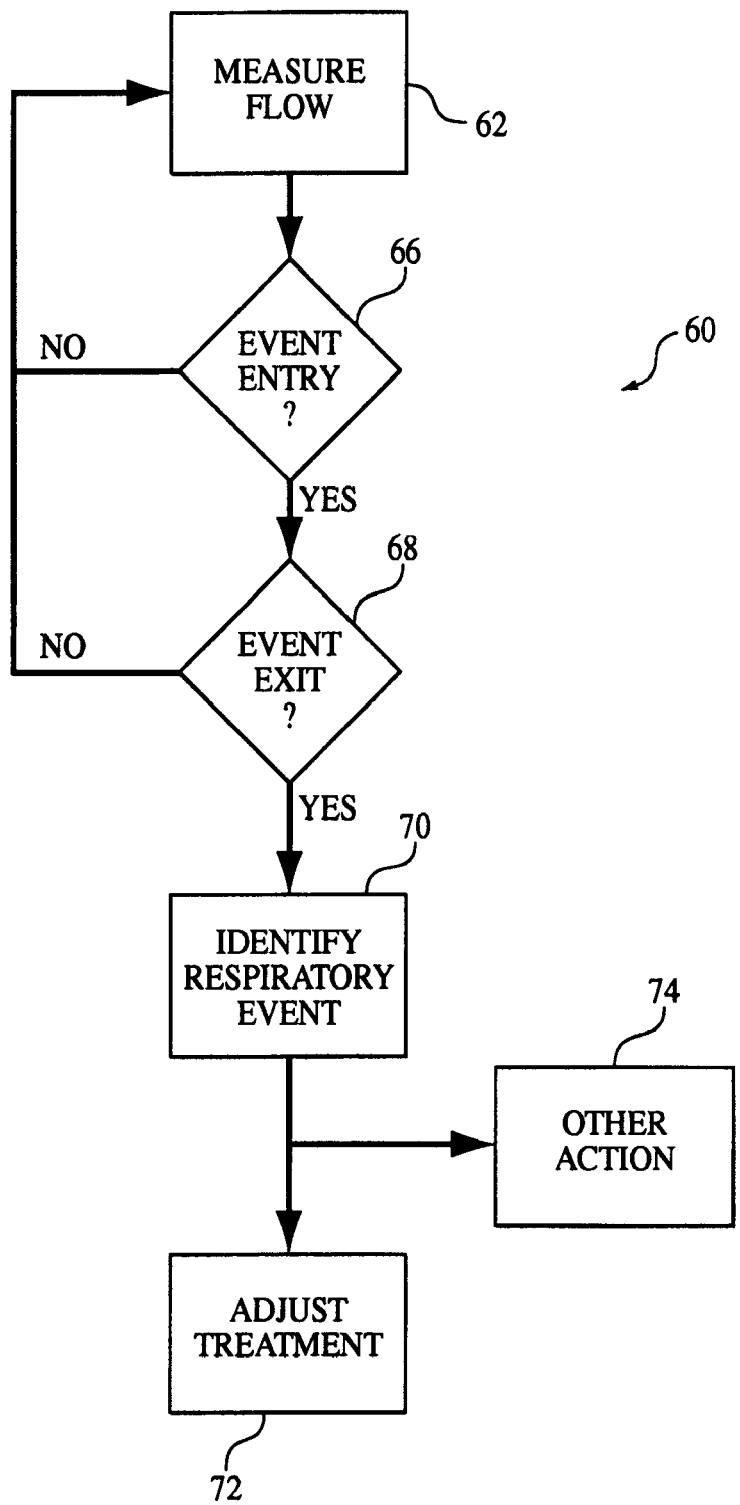
FIG. 4 is a flow chart of a method of monitoring a patient in accordance with one embodiment of the invention.

FIG. 4 is an exemplary illustration of a method 60 of monitoring and/or treating a patient. In one embodiment, the steps of method 60 are executed by processor 34. At a step 62 a flow of gas generated by respiration of the patient is determined. In one embodiment, the flow of gas is determined by flow sensor 26 as described above. At a step 66 the determined flow of the gas is monitored to identify respiratory event entries. In one embodiment, event entries are identified by event entry module 44, as was previously described. Once an event entry has been identified, method 60 proceeds to a step 68, where the determined flow of the gas is monitored to detect a respiratory event-related arousal indicative of a respiratory event exit. According to one embodiment, event exits are identified by event exit module 48, as described above. At a step 70, respiratory events are identified when an identification of an event entry is followed by an identification of an event exit. In one embodiment, respiratory events are identified by respiratory event module 54, as was explained previously.

When a respiratory event is identified at step 70, one or more aspects of a treatment being received by the patient is adjusted at a step 72. According to one embodiment, one or more aspects of the treatment are adjusted by treatment adjustment module 56, as set forth above. In one embodiment, the identification of a respiratory event may trigger one or more other actions and/or operations at a step 74. The other actions and/or operations may include recording information, keeping a count of the number of respiratory events, activating an alarm, or other actions as were provided above.

In the embodiments described above, event entry module 44 and event exit module 48 monitor the peak flow to determine whether the patient has suffered a respiratory event. The present invention also contemplates monitoring any waveform that is a surrogate for flow. For example, changes in volume inspirited or expired are directly related to the patient flow. Thus, the present invention contemplates monitoring relative changes in volume (V) as another technique for detecting respiratory events. Other known surrogates for flow include signals that change based on changes in flow, such as motor speed signals, valve position signals, temperature variations—if the temperature sensor is positioned in the flow path, and pressure variations—as pressure and flow are closely correlated.

In the embodiment discussed above, the entry and exit events are monitored by comparing the peak values of the flow parameter or flow-related parameter using a statistical analysis or threshold based analysis. For example, the present invention discussed above uses peak flows generated during successive inspirations and identifies an event exit when the determined flow indicates a general decline in the flow of gas during inspirations followed by a rapid increase in the flow of gas during inspiration. These decline and rapid increases can be detected by monitoring the relative peaks of the flow, which is a threshold based analysis, by comparing the current peaks to an average of the previous peak, which constitutes a combination of a statistical and threshold based analysis. It is to be understood that the present invention contemplates using any technique to identify the respiratory entry and exit events.

Figure 5:
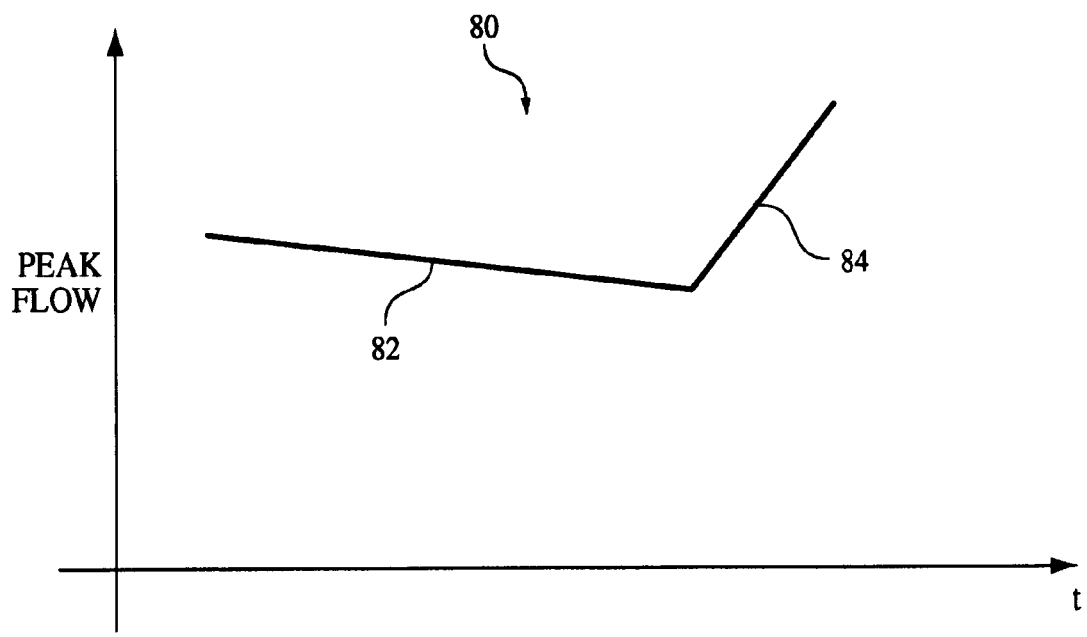
FIG. 5 is an example of templates uses to detect respiratory entry events, respiratory exit events, or both.

For example, a still further embodiment of the present invention contemplates using template matching to identify the entry events, the exit events, or both. In one embodiment, the peaks flows are compared to a template of peak flows to identify these events. FIG. 5 illustrates an exemplary peak flow template 80 for detecting a RERA event. Template 80 includes a first portion 82 that corresponds to the gradual decrease of the peak flow indicative of an entry event, i.e., region 46 in FIG. 2, and a second portion 84 that corresponds to the sharp increase in peak flow indicative of an exit event, i.e., region 50 in FIG. 2. The first portion, the second portion, or both can be used to detect the entry events, the exit events, or both. The present invention contemplates using any suitable statistical analysis to determine degree of coincidence between the measured peak flows and the peak flow templates.

Of course, the template illustrated in FIG. 5 is merely an example of one suitable template. Other shapes and configurations for the template are contemplated by the present invention, including the use of multiple templates. If multiple templates are used, the present invention contemplates that the controller select the appropriate template, for example, based on the current therapy pressures. The present invention also contemplates having the user/caregiver select the template, for example, based on how sensitive the system is to be at detecting respiratory events.

While peak flows have been described herein as a means for detecting the entry and/or exit events. Other features of the flow waveform, such as the area under the curves, or the actual flow itself can be used in either the threshold based or the template based techniques for detecting these events.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of monitoring a patient, the method comprising:
   monitoring flow of a flow of gas generated by respiration of a patient;
   detecting occurrence of a respiratory event entry based on peak values of flow during inspirations by such a patient, the detection of the occurrence of the respiratory event entry being made responsive to a decline in the peak values of flow across a first set of successive inspirations;
   detecting occurrence of a respiratory event exit based on peak values of flow during inspirations by such a patient subsequent to the first set of successive inspirations, the detection of the occurrence of the respiratory event exit being made responsive to an increase in the peak values of flow across a second set of successive inspirations; and
   identifying a respiratory event responsive to the detection of the respiratory event entry being followed by the detection of the respiratory event exit.

2. The method of claim 1, wherein monitoring the flow of the gas comprises generating a signal that corresponds to the flow of the gas, and wherein identifying the respiratory event entry comprises monitoring a shape of the signal during an inspiration.

3. The method of claim 1, wherein the second set of successive inspirations includes an inspiration from the first set of inspirations.

4. The method of claim 1, wherein detecting a respiratory event entry, detecting a respiratory event exit, or both includes comparing the peak values of flow during the first series of inspirations and/or the second series of inspirations to at least a portion of a template.

5. The method of claim 1, wherein detecting the respiratory event exit comprises detecting a change in shape of the flow of the gas during consecutive inspirations in the second series of inspirations.

6. The method of claim 1, further comprising adjusting at least one aspect of treatment received by the patient based on the identification of a respiratory event.

7. The method of claim 6, wherein the aspect of treatment comprises a pressure of gas delivered to an airway of the patient, an operation performed by a pressure generating device providing a flow of gas to the patient, or both.

8. A method of monitoring a patient, the method comprising:
   monitoring flow of gas generated by respiration of the patient;
   detecting a respiratory event based on peak values of flow during a series of inspirations that includes a first set of successive inspirations and a second set of successive inspirations, the detection of the occurrence of the respiratory event being made responsive to first a decline in the peak values of flow across the first set of successive inspirations in the series of inspirations and then an increase in the peak values of flow across the second set of successive inspirations in the series of inspirations; and
   adjusting one or more aspects of treatment received by the patient based on the identification of the respiratory event.

9. The method of claim 8, wherein the one or more aspects of treatment comprises a pressure of gas delivered to the airway of the patient.

10. A patient treatment system that delivers a pressurized flow of breathable gas to an airway of a patient, the system comprising:
    a sensor monitor that monitors flow of a flow of gas generated by respiration of a patient;
    an event entry module adapted to detect occurrences of respiratory event entries based on peak values of the flow monitored by the sensor, the event entry module being configured to detect an occurrence of a respiratory event entry responsive to a decline in the peak values of flow across a first set of successive inspirations;
    an event exit module adapted to detect occurrences of respiratory event exits that are different from the entry events based on peak values of the flow monitored by the sensor, the detection of an occurrence of a respiratory event exit being made responsive to an increase in the peak values of flow across a second set of successive inspirations, the second set of successive inspirations corresponding to a period in time that is subsequent to a period of time corresponding to the first set of successive inspirations; and
    a respiratory event module adapted to identify a respiratory event responsive to a detection of a respiratory event entry being followed by a detection of a respiratory event exit.

11. The patient treatment system of claim 10, wherein the sensor is adapted to generate a signal that corresponds to the flow of the gas, and wherein the event entry module monitors a shape of the signal during an inspiration to detect occurrences of respiratory event entries.

12. The patient treatment system of claim 10, wherein the event entry module is adapted to identify a change in shape of the flow of the gas during successive inspirations to detect respiratory event entries.

13. The patient treatment system of claim 12, wherein the event entry module is adapted to identify a change in shape of the flow of the gas during successive inspirations to detect respiratory event entries.

14. The patient treatment system of claim 10, wherein the event exit module is adapted to identify a change of shape of the flow of the gas during consecutive inspirations.

15. The patient treatment system of claim 10, further comprising a treatment adjustment module that adjusts one or more aspects of treatment received by the patient, an operation performed by a pressure generating device providing a flow of gas to the patient, or both based on the identification of a respiratory event.

16. The patient treatment system of claim 15, wherein the treatment adjustment module adjusts a pressure of gas delivered to the airway of the patient with the respiratory event module identifies a respiratory event.

17. The patient treatment system of claim 10, wherein (a) the event entry module is adapted to detect respiratory event entries by comparing peak values of flow during inspirations to at least a portion of a template, (b) the event exit module is adapted to detect respiratory event exits by comparing peak values of flow during inspirations at least a portion of a template, or (c) both (a) and (b).

* * * * *